(12) United States Patent
Janszen

(10) Patent No.: US 6,200,250 B1
(45) Date of Patent: Mar. 13, 2001

(54) DIAPERS WITH MOISTURE DETECTION AND PROCESS AND APPARATUS FOR MAKING THEM

(75) Inventor: David Janszen, Columbus, OH (US)

(73) Assignee: Knox Security Engineering Corporation, Stamford, CT (US)

( * ) Notice: Subject to any disclaimer, the term of this patent is extended or adjusted under 35 U.S.C. 154(b) by 0 days.

(21) Appl. No.: 09/046,468

(22) Filed: Mar. 23, 1998

Related U.S. Application Data

(63) Continuation-in-part of application No. 08/646,453, filed on May 7, 1996, now Pat. No. 5,760,694.

(51) Int. Cl.[7] .................. B31B 1/68; A61F 13/15
(52) U.S. Cl. .................... 493/383; 493/334; 493/938; 604/361
(58) Field of Search .................... 493/328, 334, 493/374, 383, 379, 938; 604/358, 361

(56) References Cited

U.S. PATENT DOCUMENTS

| | | | |
|---|---|---|---|
| 5,760,694 | * 6/1998 | Nissim et al. ............. | 604/361 |
| 5,790,036 | * 8/1998 | Fisher et al. ............. | 604/361 |
| 5,817,076 | * 10/1998 | Fard ........................ | 604/361 |
| 5,838,240 | * 11/1998 | Johnson .................... | 604/361 |
| 5,908,411 | * 6/1999 | Matsunari .................. | 604/361 |
| 5,947,943 | * 9/1999 | Lee ......................... | 604/361 |

\* cited by examiner

*Primary Examiner*—Brian L. Johnson
*Assistant Examiner*—Matthew Luby
(74) *Attorney, Agent, or Firm*—Stanger & Dreyfus, P.C.

(57) ABSTRACT

A method of manufacturing a diaper includes constructing a backing sheet having an exterior surface and an interior surface so a to form an exterior of the diaper and an interior of the diaper, bonding a tissue layer to the interior surface of the backing sheet, bonding an elastic pouch to the exterior surface of the backing sheet to contain a detector module, and placing sensing electrodes within the interior of the diaper along the interior surface of the backing sheet in contact with the tissue layer that is bonded to the backing sheet, and in a direction to extend opposite the elastic pouch that is bonded to the outside of the backing sheet so as to allow the sensing electrodes to couple capacitively to the sensor module.

18 Claims, 14 Drawing Sheets

DIAPERS WITH MOISTURE DETECTION AND PROCESS AND APPARATUS FOR MAKING THEM

RELATIVE APPLICATIONS

This application is a continuation-in-part of application Ser. No. 08/646,453, filed May 7, 1996, now U.S. Pat. No. 5,760,694.

FIELD OF THE INVENTION

This invention relates to diapers with devices for monitoring wetness, and particularly to processes and apparatuses for constructing such diapers.

BACKGROUND OF THE INVENTION

Various diapers have been developed with means for monitoring moisture or wetness. In diapers, the purpose of such devices is to set off an alarm when a diaper becomes wet. This permits a parent or other attendant to tend to a newborn infant or toddler. However such devices have disadvantages in that they may require current-carrying conductors to pass mechanically through the diaper's plastic outer sheath, may subject the skin of the wearer to direct voltages from a voltage source, may be sensitive only in a limited area, may accidentally respond to the wearer sitting on a wet or metal bench or park slide, or have other drawbacks.

SUMMARY OF THE INVENTION

An embodiment of the invention involves constructing a diaper that has internal electrodes for sensing wetness that are in contact with one or more elements of the absorbent material within a diaper, and an external holder to retain a detector module that is dielectrically isolated from the internal electrodes, and that allows non-conductive coupling between the detector module and the internal sensing electrodes.

According to an embodiment of the invention, the sensing electrodes are placed within a diaper to project along the interior surface of the backing sheet in contact with a tissue layer that is bonded to the backing sheet and extend opposite an elastic pouch that is bonded to the outside of the backing sheet. The pouch contains a detector module capacitively coupled to the electrodes.

The various features of novelty which characterize the invention are pointed out in the claims forming a part of this specification. Objects and advantages of the invention will become evident from the following detailed descriptions of embodiments of the invention when read in light of the following drawings.

DETAILED DESCRIPTION OF PREFERRED EMBODIMENTS

Figure 1A:
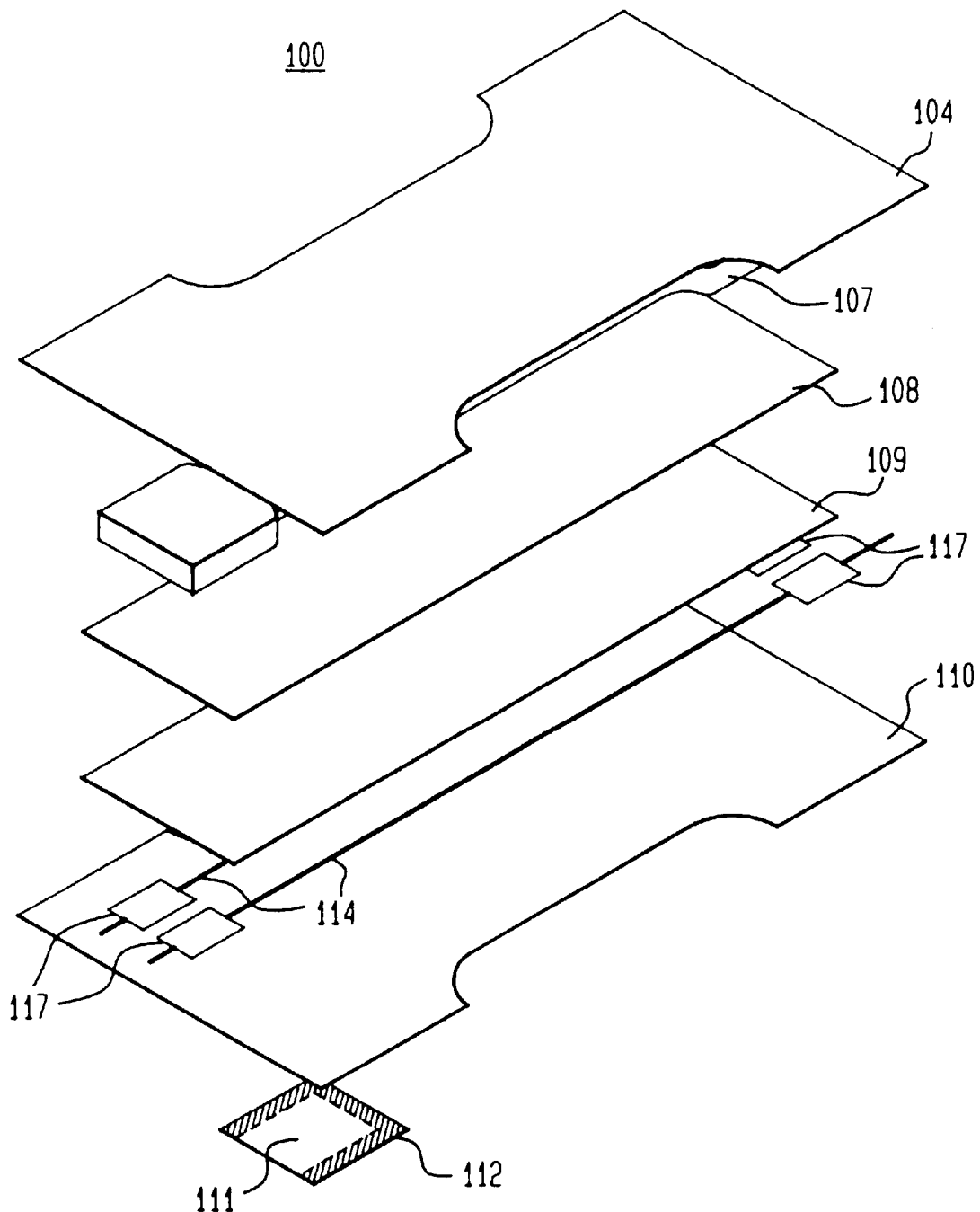
FIGS. 1A and 1B are exploded perspective views of a diaper conveying two embodiments of the invention.

In the exploded perspective view of FIG. 1A, a disposable diaper 100 includes an inner sheet 104 of a water-permeable film, generally known and hereinafter referred to as cover stock 104, that overlies a wetness absorber layer 107 of highly liquid-absorbent padding or other highly absorbent material, generally known and hereinafter referred to as the core 107. In one embodiment the core 107 may include granules or filaments of water-retentive polymer, such as polyacrylic acid. An outer, electrically insulating plastic film that is impermeable to liquid water, generally known and hereinafter referred to as the backing sheet 110, supports two conductive spaced-apart electrodes 114, in the form of metallic or other electrically-conductive strips, with low surface area, hereinafter referred to as the sensing electrodes 114, that extend along the center of the backing sheet 110. The backing sheet 110 also supports a tissue 108 and a barrier 109. According to embodiments of the invention, the sensing electrodes 114 electrically contact the core 107, or the tissue 108, or the barrier 109. According to an embodiment of the invention, the sensing electrodes 114 pass longitudinally through the core 107. According to another embodiment, sensing electrodes 114 project along the interior surface of the backing sheet 110 in contact with the core 107. According to another embodiment, the sensing electrodes 114 are in the form of conductive filaments, threads or wires.

The sensing electrodes are connected electrically to widened conductive areas 117, hereinafter referred to as coupling electrodes 117, that serve to couple signals between the sensing electrodes 114 and a detector module that is to be placed against the outer surface of the backing sheet 110. The detector module is provided with pickup electrodes each of which couples non-conductively, for example capacitively, to respective coupling electrodes 117.

An optional tissue layer 108 may be in contact with the core 107, that serves to distribute wetness more quickly and uniformly about the core 107, and that also serves to bring wetness from core 107 into close contact with sensing electrodes 114.

An optional wetness barrier layer 109 may be interposed between a portion of the sensing electrodes 114 and the core 107 or the tissue 108, that may serve to prevent wetness in the core 107 from reaching a defined portion of the sensing electrodes 114. If barrier layer 109 is soluble in water, the effect will be a delay before wetness reaches the covered portion of the sensing electrodes 114. If barrier layer 109 is not soluble in water, the effect will be a requirement that the wetness in the core 107 reaches beyond the covered portion of the sensing electrodes 114 before the wetness may be detected.

Pocket slip 112 is bonded to backing sheet 110 along all but one of its edges to as to form the pocket 111. The pocket 111 is positioned so that when a detector module is placed therein, the pickup electrodes in the pocket 111 are registered opposite the coupling electrodes 117. The bonded area of pocket slip 112 is identified with cross-hatching. If pocket slip 112 is composed of material that is resilient, then insertion of an item that is slightly larger than the relaxed size of the pocket 111 into the pocket 111 will deform the unbonded portion of pocket slip 112, which will tend to hold such an inserted item snugly in place and apply tension to the area of backing sheet 110 located beneath the unbonded portion of pocket slip 112. If pocket slip 112 is composed of an inelastic material, then the same tension and secure insertion may be obtained by a combination of deformation of the backing sheet 110 and deformation of the inserted item itself. According to one embodiment, one pair of the coupling electrodes 117 and one pocket 111 is located near either the front or the rear waistband of the diaper 100, and in another embodiment, a separate set of these aspects is located near both waistbands.

Figure 1B:
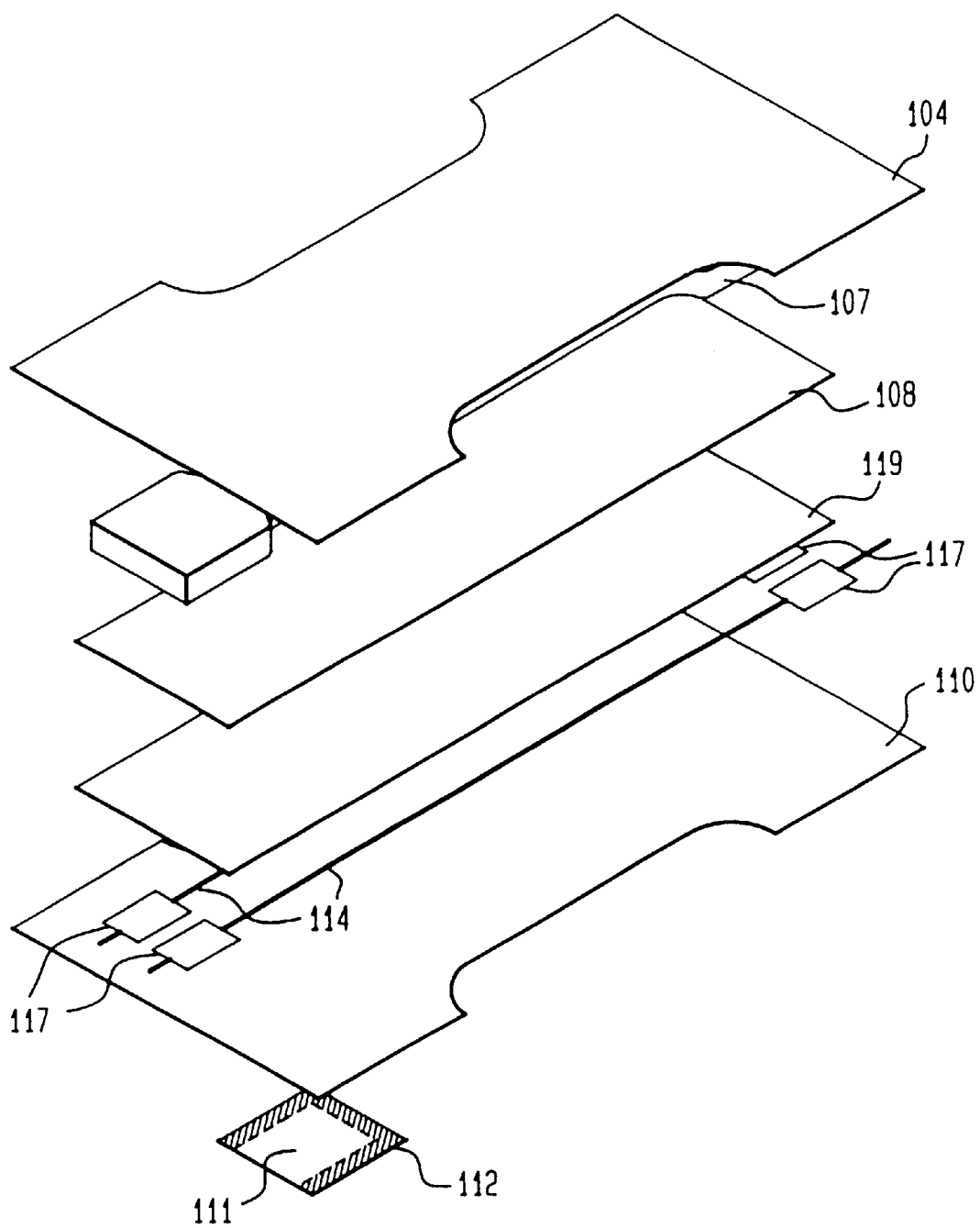

In the exploded perspective view of FIG. 1B, a disposable diaper 100 includes a sensor carrier layer 119, onto which the sensing electrodes 114 and coupling electrodes 117 may be printed or otherwise pre-assembled prior to assembly onto backing sheet 110.

FIGS. 2A, 2B, 2C, and 2D show four possible arrangements of sensing and coupling electrodes 114 and 117. These represent repeated patterns that are to be parted at the separation line 140. The separation line 140 may correspond to the place where the diapers 100 made in the machine direction are separated from one another near the end of the production line, or where sets of electrodes 114 and 117 that are printed or otherwise pre-assembled onto a carrier layer are separated prior to placement onto the backing sheet 110, or the separation line 140 may simply be conceptual, where electrodes 114 and 117 are assembled repeatedly onto a diaper that is made in the cross-direction.

Figure 2A:
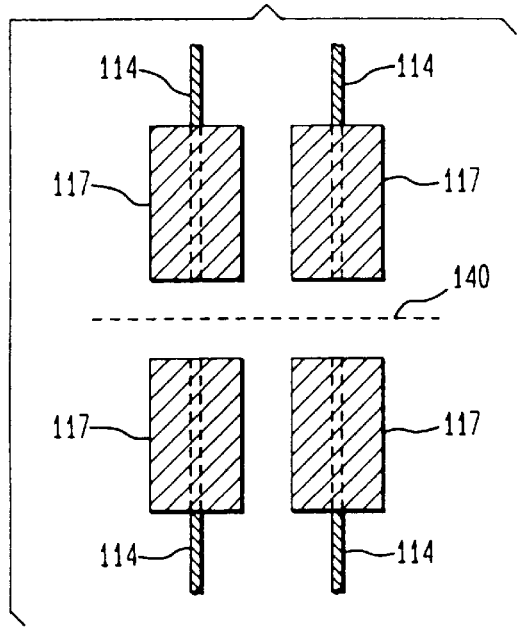
FIGS. 2A, 2B, 2C, and 2D are plan views of surfaces that bear electrode arrangements corresponding to several embodiments of the invention.
Figure 2B:
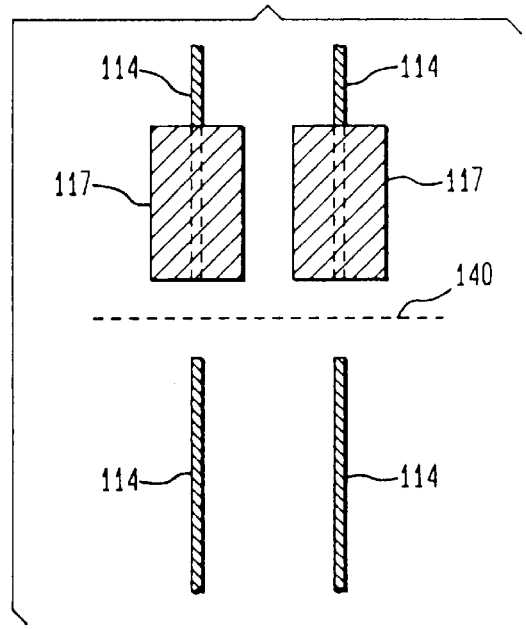
Figure 2C:
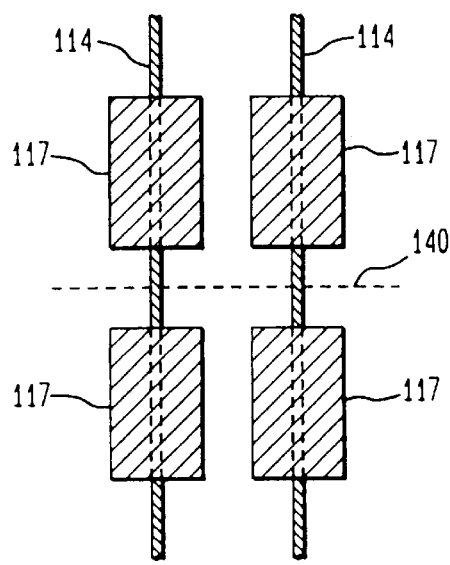
Figure 2D:
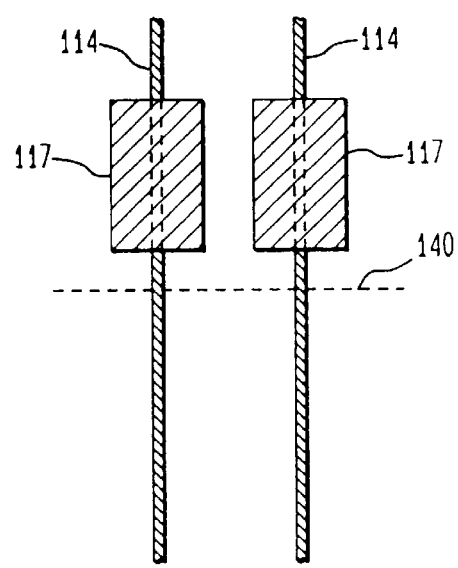

In FIG. 2A, sensing electrodes 114 are discontinuous, and there are two pair of coupling electrodes 117 for each pair of sensing electrodes 114. This provides a pair of coupling electrodes near each waistband. In FIG. 2B, sensing electrodes 114 are also discontinuous, but there is one pair of coupling electrodes 117 for each pair of sensing electrodes 114. This provides a pair of coupling electrodes near only one waistband. In FIG. 2C, sensing electrodes 114 are continuous, and there are two pair of coupling electrodes 117 for each pair of sensing electrodes 114. This provides a pair of coupling electrodes near each waistband. In FIG. 2D, sensing electrodes 114 are also continuous, but there is one pair of coupling electrodes 117 for each pair of sensing electrodes 114. This provides a pair of coupling electrodes near only one waistband.

The sensing electrodes 114 may be filaments, wires, yarn, ribbon, foil, fabric or film made from conductive material. The sensing electrodes 114 may be filaments, yarn, ribbon, fabric or film that bears conductive filler material, that is coated with conductive material, or with surfaces subjected to a conversion process or suffused with a material that renders said surfaces conductive. The sensing electrodes 114 may be in the form of yarn that includes continuous or discontinuous lengths of conductive filament or wire, that is wrapped with conductive filament or wire, that is infused with material that is conductive, or that is infused with material that bears conductive filler material. The sensing electrodes 114 may be liquid or plastic material that is conductive or that bears conductive filler material, such as a thermoplastic, wax, paste, gel, latex, adhesive, or ink, that may be selectively applied onto a surface or into an absorbent matrix by methods such as printing, rolling, or extrusion.

Sensing electrodes 114 may be formed by the selective conversion or suffusion of portions of a surface of a film, fabric or tissue material by a process that renders said portions conductive. Sensing electrodes 114 may be formed by the selective removal of continuous conductive coating or converted outer layer from surface of a film material such as by abrasion or photolithography to render multiple isolated conductive areas (electrodes) from a continuous piece of coated film. Sensing electrodes 114 may be formed by the selective removal of portions of an electrode film, fabric or tissue material such as by die-cutting to render multiple isolated conductive elements (electrodes) from a continuous element of coated film, fabric or tissue material.

Sensing electrodes 114 may be redundant, in that each of the two electrodes that make up a pair may have more than one strand, ribbon, strip, etc., and that these redundant elements may be of different morphologies.

The coupling electrodes 117 may be ribbon, foil, fabric, tissue or film made from conductive material. The coupling electrodes 117 may be ribbon, fabric, tissue or film that bears conductive filler material, that is coated or infused with conductive material, or with surfaces subjected to a conversion process or suffused with a material that renders said surfaces conductive. The coupling electrodes 117 may be ribbon, fabric, tissue or film material that is conductive or has one or both surfaces made conductive, where said structure is optically transparent or translucent. The coupling electrodes 117 may be liquid or plastic material that is conductive or that bears conductive filler material, such as a thermoplastic, wax, paste, gel, latex, adhesive, or ink, that may be selectively applied onto a surface or into an absorbent matrix by methods such as printing, rolling, or extrusion.

The coupling electrodes 117 may be formed by the selective conversion or suffusion of portions of a surface of a film, fabric or tissue material by a process that renders said portions conductive. The coupling electrodes 117 may be formed by the selective coating of portions of a surface of a film, fabric or tissue material with conductive material, such as by sputtering or thermal vapor deposition. The coupling electrodes 117 may be formed by the selective removal of continuous conductive coating or converted outer layer from surface of a film material to render multiple electrodes from a continuous piece of coated film. The coupling electrodes 117 may be formed by the selective removal of portions of an electrode film, fabric or tissue material such as by die-cutting to render multiple electrode elements from a continuous element of coated film.

Figure 3A:
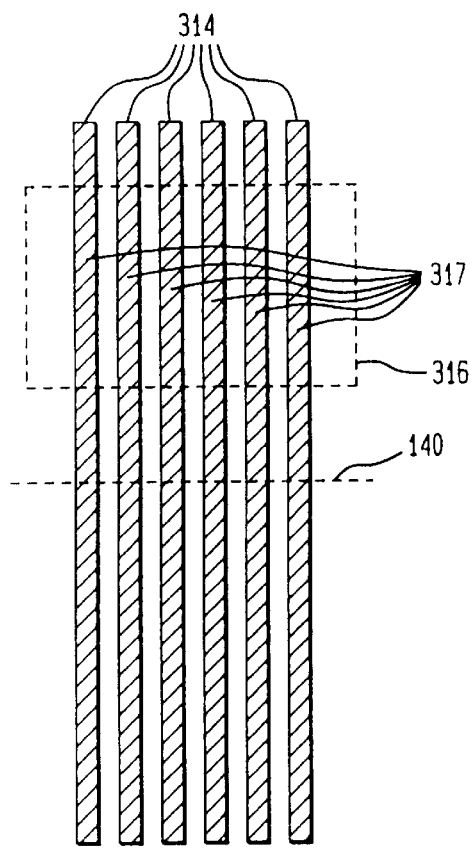
FIGS. 3A and 3B are plan views of surfaces that bear electrode arrangements corresponding to other embodiments of the invention.
Figure 3B:
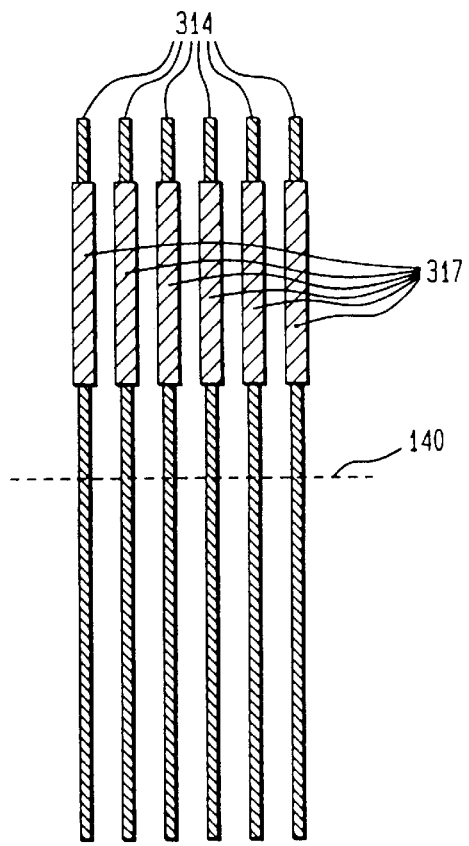

FIGS. 3A and 3D depict two embodiments of an electrode arrangement where a plurality of individual electrodes 314 and 317 may function together to effectively form pairs of electrodes corresponding to sensing electrodes 114 and coupling electrodes 117 in FIGS. 1 and 2. In FIG. 3A, the electrodes are of uniform width, where the portions of these electrodes that are to function as the coupling electrodes 317 are the portions that are located in coupling area 316. In FIG. 3B, the sensing electrodes 314 are narrower than coupling electrodes 317. The arrangement of the electrodes into a plurality of parallel elements serves to provide great immunity to translational variation in the registration between the pocket 111 and the coupling electrodes 317.

Figure 4:
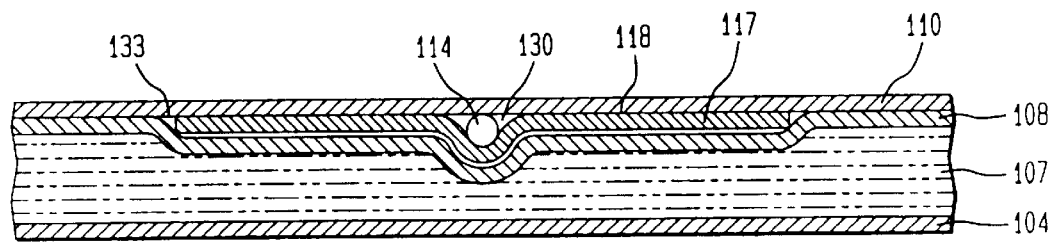
FIG. 4 is an elevation of an electrode arrangement corresponding to an embodiment of the invention.
Figure 5:
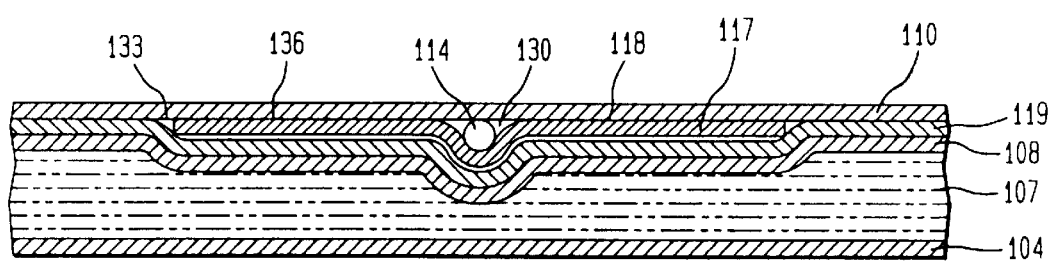
FIG. 5 is an elevation of an electrode arrangement corresponding to another embodiment of the invention.
Figure 6:
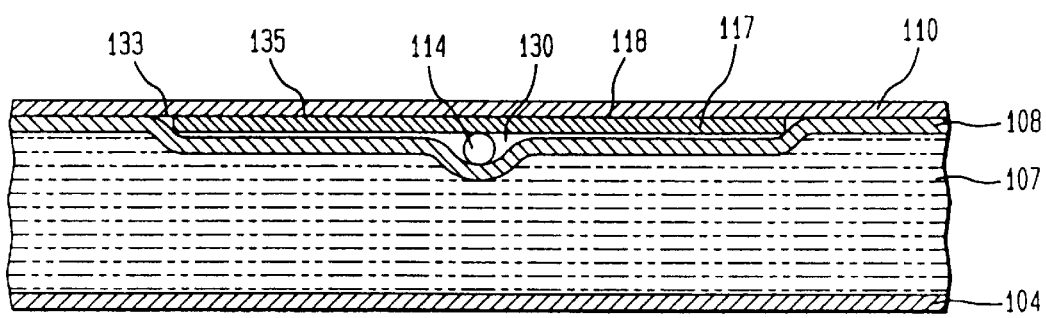
FIG. 6 is an elevation of an electrode arrangement corresponding to another embodiment of the invention.

FIGS. 4, 5, and 6 depict three possible construction schemes pertaining to the placement of the electrodes relative to the other layers in the diaper 100. Each figure is an elevation that cuts across a single coupling electrode 117 in a direction orthogonal to the sensing electrode 114, and that includes all layers but the pocket 111. These are simplified to the extent that certain adhesive applications and other typical or possible processes are not depicted, and no indication is given as to the treatment of the various layers as they exist beyond the boundaries of the drawn area.

In FIG. 4, the backing sheet 110 has been sprayed with the construction adhesive 133, has had the sensing electrode 114 laid down into the construction adhesive 133, has had the coupling electrode 117, which is oriented so that the conductive coating 118 is facing the sensing electrode 114, nipped down against the sensing electrode 114, has had the tissue 108 nipped down over both electrodes 114 and 117, has had the core 107 nipped down over the tissue 108, and finally had the cover 107 nipped down over the core 107. This is the first preferred embodiment.

An electrically conductive liquid, paste, putty, or powdered solid material may be deposited in the gap 130 in contact with the sensing electrode and the coupling electrode.

FIG. 5 differs from FIG. 4 only in that barrier layer 119 is added between tissue 108 and sensing and coupling electrodes 114 and 117.

In FIG. 6, the side of the sensing electrode 114 that bears the adhesive 135 has been nipped down to the backing sheet 110, and the side with the conductive coating 118 faces outward. The tissue 108 has been sprayed with the construction adhesive 133, and the sensing electrode 114 has been laid down into the construction adhesive 133 in the tissue 108, whereupon the tissue 108 bearing the sensing electrodes 114 has been nipped down to the backing sheet 100 that bears the coupling electrodes 117. This places the conductive coating 118 on the coupling electrodes 117 in contact with sensing electrodes 114. The core 107 is nipped down onto the existing structure, and ultimately the cover 104 is nipped down over this.

An electrically conductive liquid, paste, putty, or powdered solid material may be deposited in the gap 130 in contact with the sensing electrode and the coupling electrode.

Figure 7:
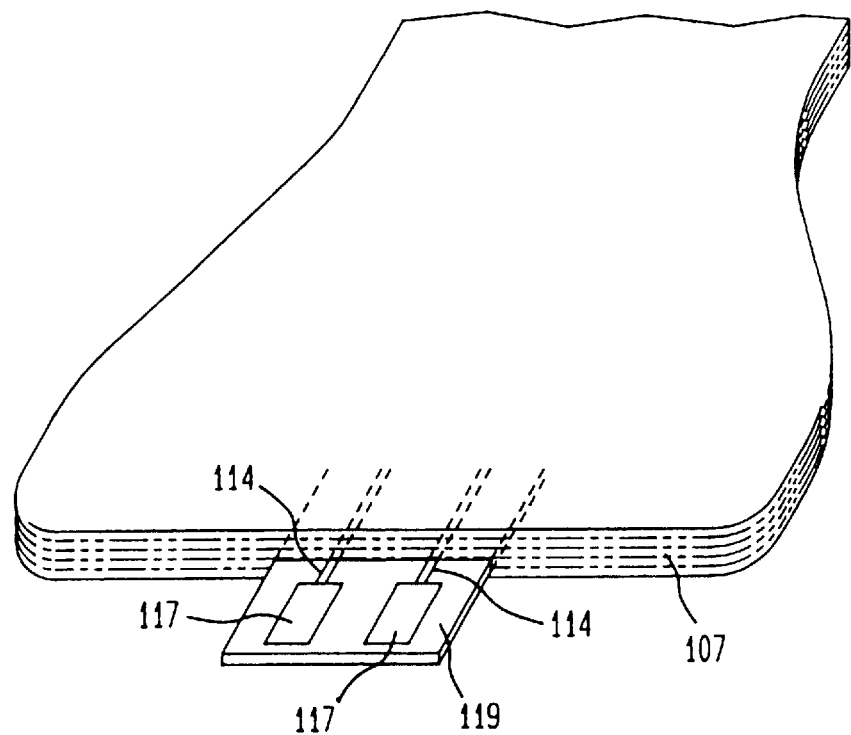
FIG. 7 is a perspective view of an electrode arrangement corresponding to another embodiment of the invention.
Figure 8:
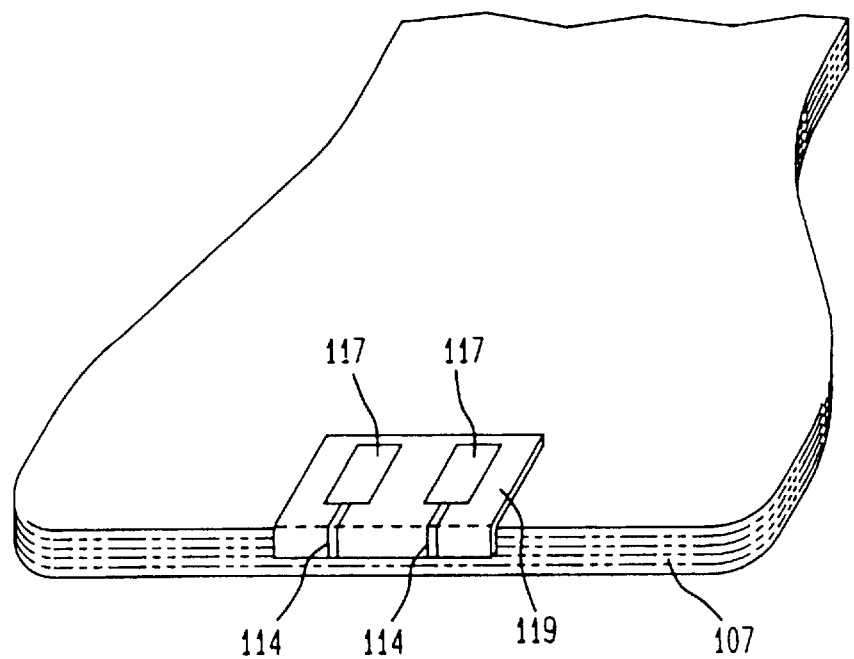
FIG. 8 is a perspective view of an electrode arrangement corresponding to another embodiment of the invention.

FIGS. 7 and 8 depict two possible arrangements of sensing and coupling electrodes 114 and 117 where they are incorporated into the core 104. In both cases, sensing and coupling electrodes 114 and 117 are printed or otherwise pre-assembled onto a carrier layer 119, and placed within the core 104, with the ends bearing coupling electrodes 117 protruding from its ends. In FIG. 7, the coupling electrodes 117 are to be assembled to the backing sheet 110 in an area near the waistband that is clear of the core 104. In FIG. 8, the portion of carrier 119 that bears the coupling electrodes 117 is folded back over the core and is therefor located beneath the core in the finished diaper 100.

In another embodiment, unsupported sensing electrodes 114 are laid into the core 107, and the coupling electrodes are brought down over them as in FIG. 4.

Figure 9:
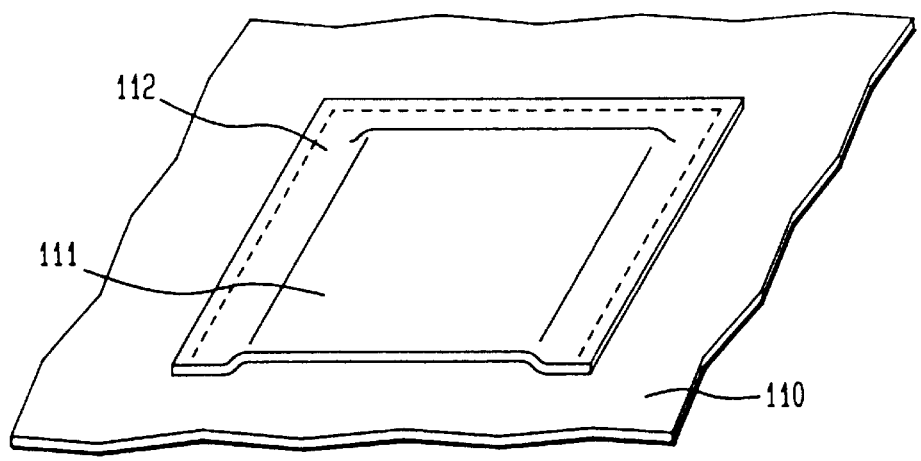
FIG. 9 is a perspective view of a pocket with aspects embodying the invention.

FIG. 9 is a detail of the pocket 111 bonded to the backing sheet 110, showing the bonded area around all but one edge of the pocket slip 112.

Figure 10:
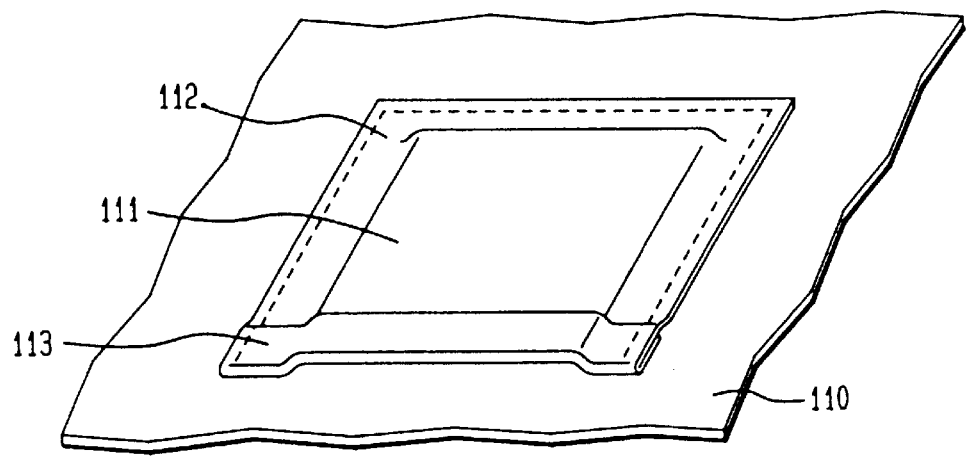
FIG. 10 is a perspective view of a pocket with a further aspect embodying the invention.

FIG. 10 is the same as FIG. 9, except that one method of reinforcement of the unbonded edge of pocket 111 is illustrated, where the edge 113 that is not to be bonded to the backing sheet 110 is folded over on itself one or more times and bonded to itself prior to or concurrent with the bonding of the pocket 111 to the backing sheet 110. In another embodiment, the open edge of the pocket 111 is reinforced by bonding a separate strip of material to it.

Figure 11:
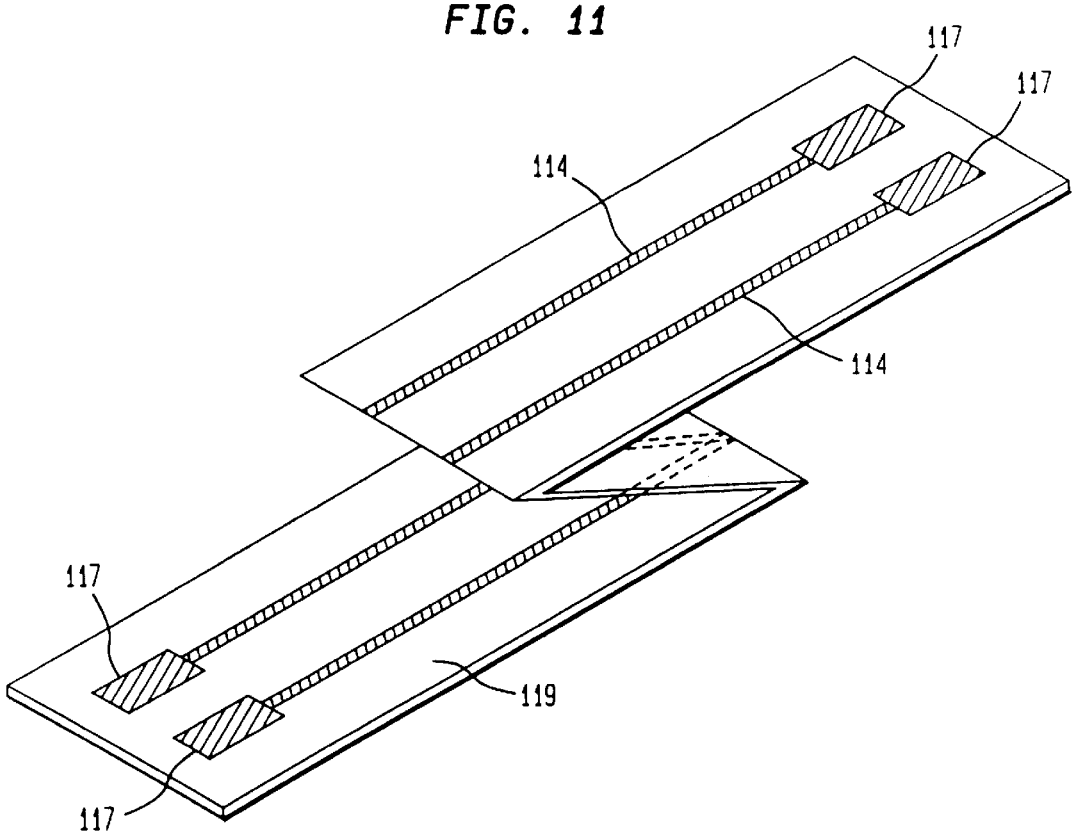
FIG. 11 is a perspective view illustrating the folding of a sensor element to shorten its effective length.

FIG. 11 depicts the folding of the carrier strip 119 bearing electrodes 114 and 117 so as to shorten its length. The Z-fold can be placed into the material as it is being assembled onto the diaper 100, or prior to assembly.

Figure 12:
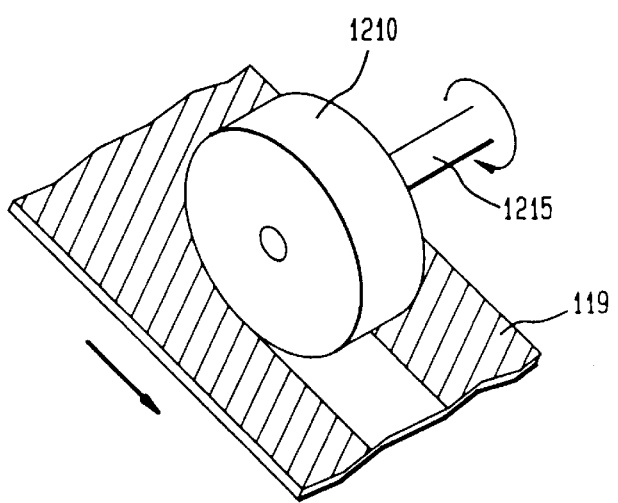
FIG. 12 is a perspective view illustrating an apparatus for the removal of a coating from an area of coated film.

FIG. 12 depicts an apparatus 1215 for abrading the conductive coating 118 from the carrier strip 119. Here, the rubber wheel 1210 rotates so that it rubs the carrier strip 119 counter to its direction of travel.

Figure 13A:
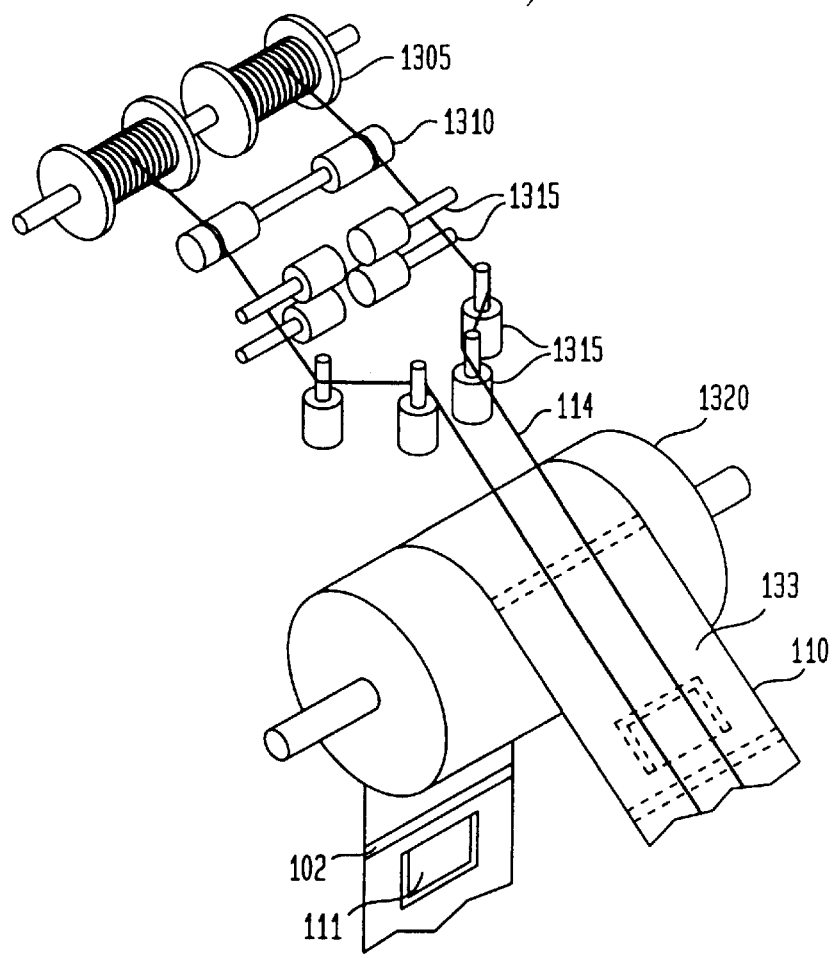
FIG. 13A is a perspective view illustrating an apparatus for the placement of the sensing electrodes onto a diaper backing sheet web.

FIG. 13A depicts an apparatus for applying the sensing electrodes 114 into the construction adhesive 133 on the backing sheet 110. Reels of wire 1305 are fitted with appropriate feed, braking and anti-run-on means. Sensing electrodes 114 in the form of wires take one or more turns around tensioning drums 1310, thread through direction control pins 1315, and are drawn onto backing sheet web 110 by the motion of said web on a roller 1320. Also depicted for clarity are pockets 111, and frontal tape 102.

Figure 13B:
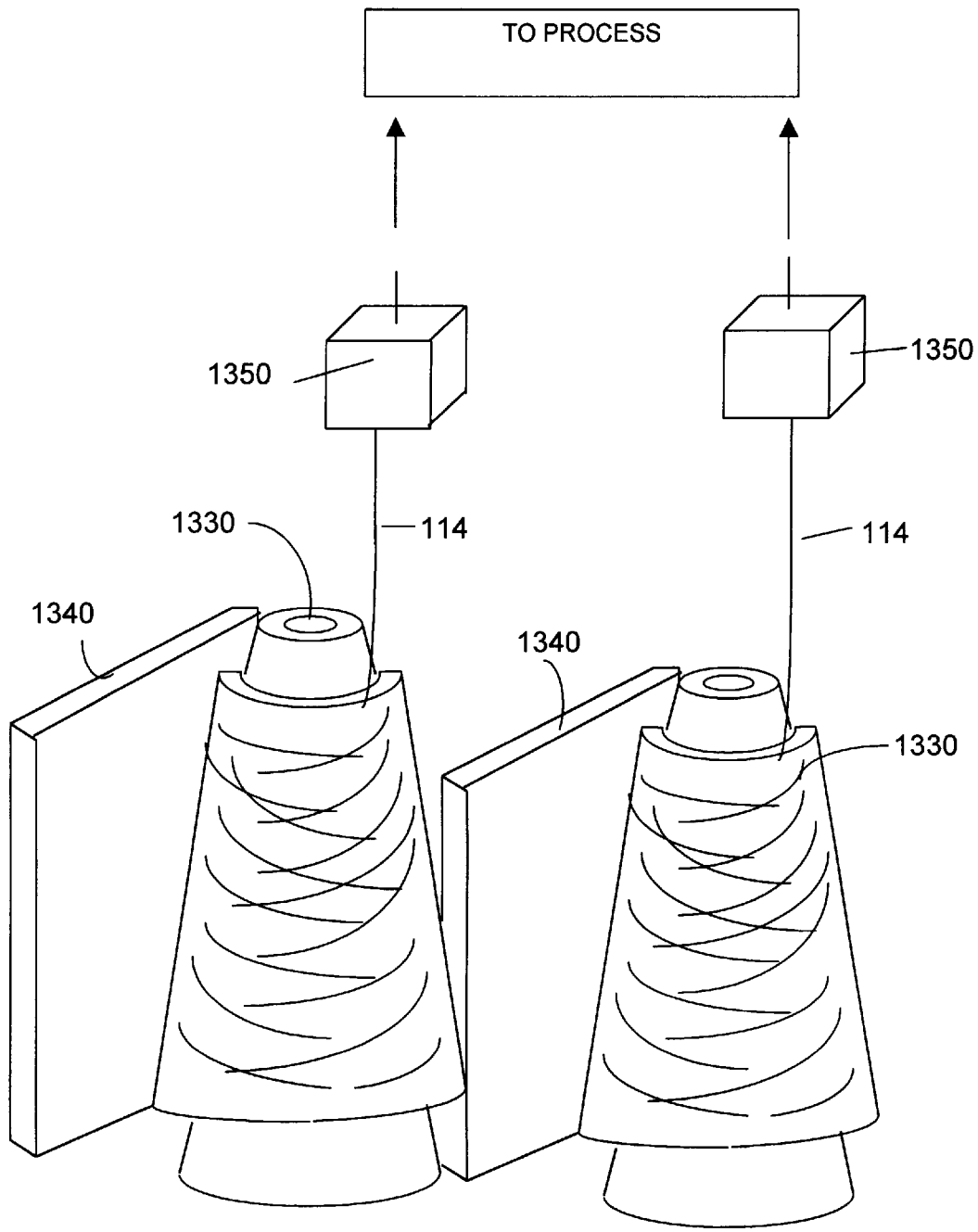
FIG. 13B is a perspective view illustrating another apparatus for the placement of the sensing electrodes onto a diaper backing sheet web.

FIG. 13B depicts an apparatus for feeding the sensing electrodes 114 into the diaper manufacturing process. Stationary bobbins of wire 1330, typically cone-shaped, are fitted with shoes 1340 that serve to prevent the sensing electrodes 114 from uncoiling from bobbins 1330 under slack conditions. This is important when the sensing electrodes 114 are made from very fine wire that may have a tendency to spring from the bobbins 1330 and become difficult to recover. Sensing electrodes 114 proceed through the tensioning means 1350 and on into the manufacturing process.

Figure 14:
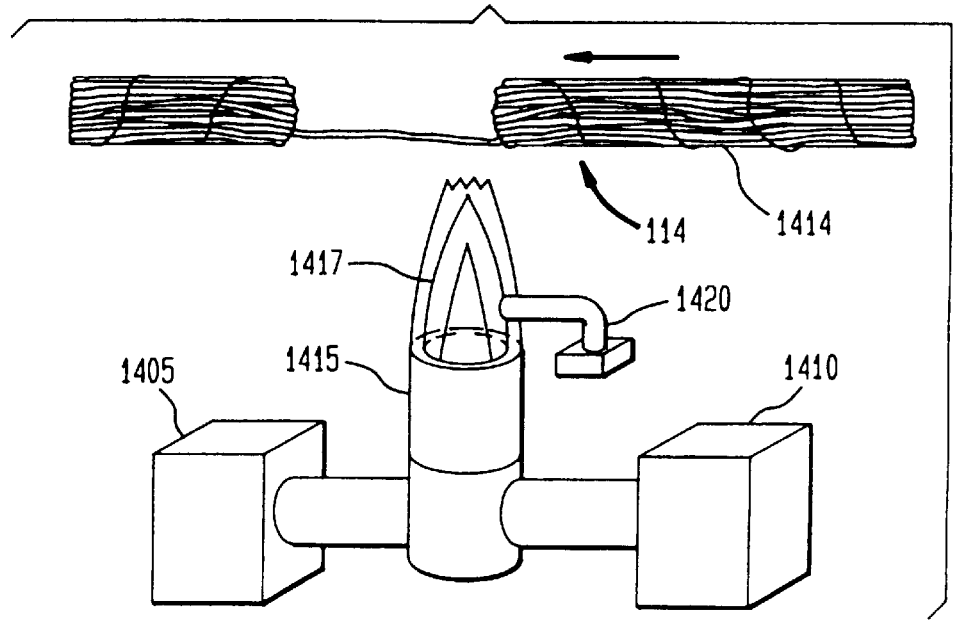
FIG. 14 is a perspective view illustrating an apparatus for the removal of non-conductive fibers from a wire-wrapped yarn.

FIG. 14 depicts an apparatus for removing the non-conductive fibers from the core of a yarn 1414 that has been spun-wrapped with wire to form an electrode 114. Gaseous fuel source 1405 feeds gas to burner 1415. Gas flow modulator 1410 is connected in parallel with gas source 1405. Ignition source 1420 may ignite flame 1417. The yarn 1414 is drawn through the space directly over the flame, and the flame is modulated so that it vaporizes, melts, or partially vaporizes and partially melts the non-conductive fibers in the core of the yarn. The resultant segments of bare wire can make improved contact with conductive surfaces, such as coupling electrodes 117.

Figure 15:
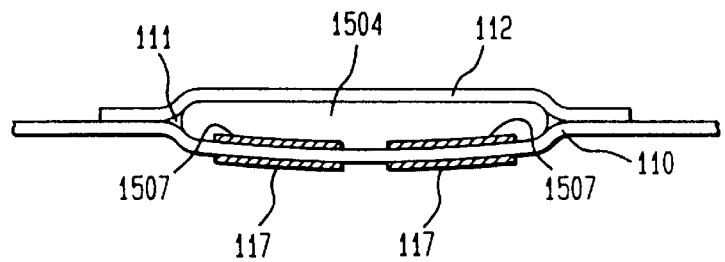
FIG. 15 is a sectional view illustrating an example of a module in a pocket on the back of a diaper.

FIG. 15 illustrates an example of a module 1504 having pickup electrodes 1507 in the pocket 111 formed by the pocket slip 112 on the backing sheet 110. The pickup electrodes 1507 are positioned opposite, and are here non-conductively and capacitively coupled to, the coupling electrodes 117 across the backing sheet 110. Thicknesses are exaggerated for clarity.

Figure 16:
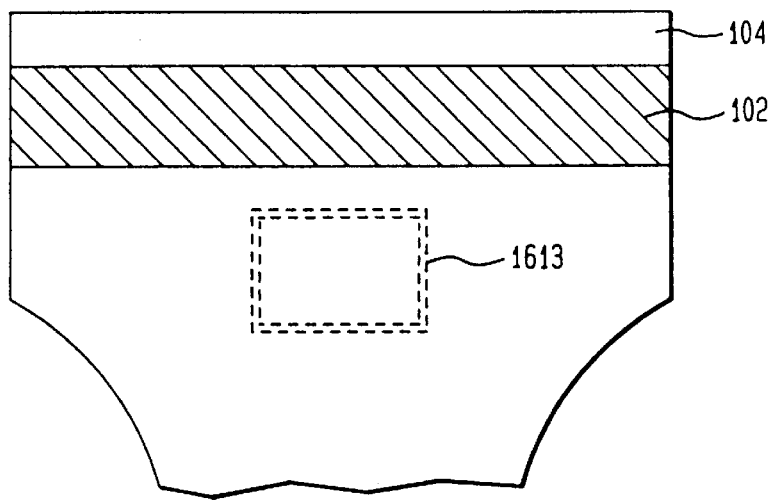
FIG. 16 is a plan view of the frontal area of a diaper having a cloth-like backing sheet and a treated rectangular portion.
Figure 17:
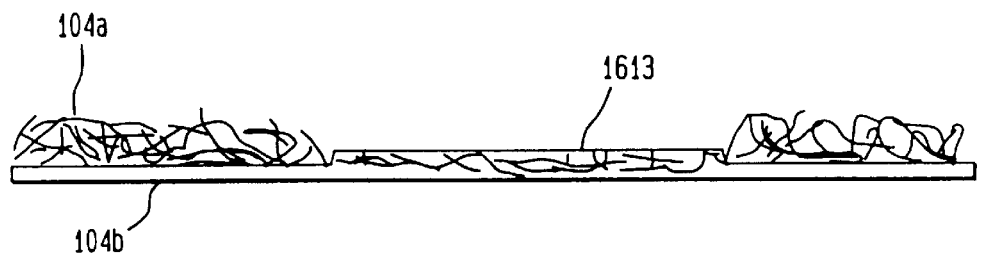
FIG. 17 is a sectional view through an area of cloth-like backing sheet containing a treated portion.

FIGS. 16 and 17 depict a portion of an embodiment of the backing sheet 110 in the form a typical two-component cloth-like sheet 110, composed of a non-woven fabric layer 110A and a film layer 110B, and containing a rectangular treated portion 1613. The treated portion 1613 includes a monolithic matrix of the non-woven fabric layer 110A and the film layer 110B. The treatment serves to increase the dielectric constant and decrease the thickness of the treated portion 1613, and to render it more amenable to later bonding of the pocket material. The treatment of the portion 1613 may be accomplished thermally or ultrasonically, but the preferred method is ultrasonic.

In FIG. 16, the treated portion 1613 is located centrally and near the front of the waistband, as indicated by the presence of the frontal tape 102. According to other embodiments the treated area is alternatively or additionally located near the rear waistband or on another part of the diaper. For a given diaper construction, the position of the treated portion 1613 will tend to coincide with that of the pocket 111 that is shown in various other figures.

FIG. 17 show the fibers of the backing sheet non-woven layer 110A separate from and randomly oriented over the backing sheet film layer 110B, except in the treated portion 1613. There, the two materials are shown combined into a monolithic matrix.

In addition to backing sheet film 110B, the embedding encapsulant, according to embodiments of the invention, includes another material added to either side of the portion 1613 prior to treatment. This additional material may be a thermoplastic film that is compatible with the backing sheet film 110B, or it may be some other material that could serve the purpose of increasing the fraction of solid thermoplastic available to encapsulate the fibers of the non-woven backing sheet layer 110A.

Figure 18:
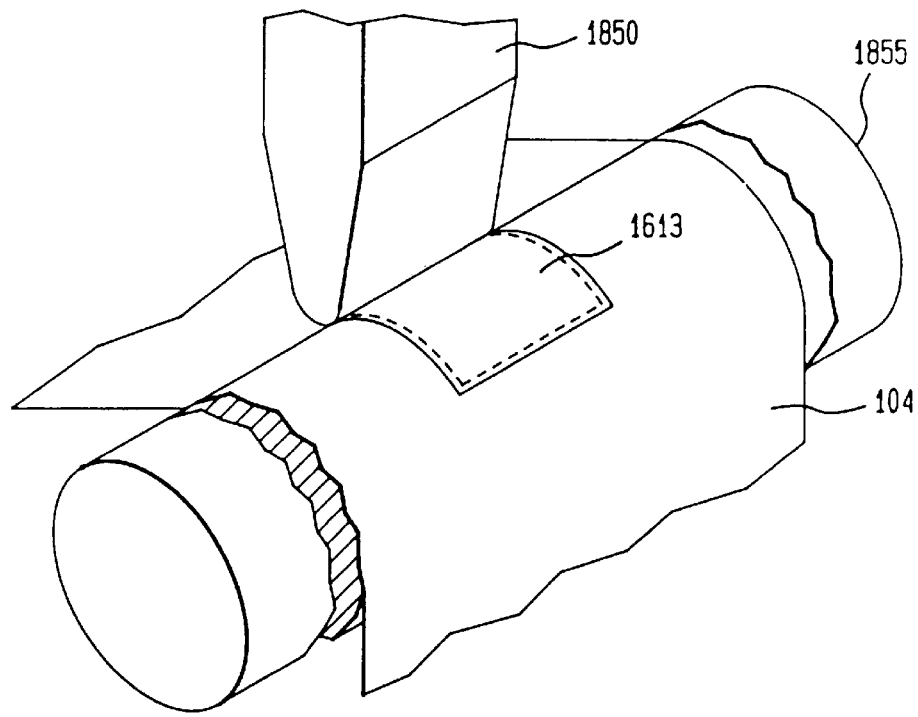
FIG. 18 depicts an ultrasonic apparatus for processing of the treated portion of FIGS. 16 and 17.

FIG. 18 depicts the basics of an ultrasonic apparatus for performing the treatment of the portion 1613. The backing sheet 110 is conveyed continuously on the roll 1855 with the non-woven layer 110B typically facing the ultrasonic horn 1850. The ultrasonic horn 1850 is powered periodically, so that it supplies energy across its width to the backing sheet 110 for uniform time periods at uniform time intervals. This is done to assure that uniform lengths of a narrow portion of the overall width of the backing sheet 110 are subjected to treatment at uniform spatial intervals. According to an embodiment of the invention, a rotary horn is used as an alternative to a stationary horn in order to eliminate the risk of the backing sheet 110 becoming snagged on the horn.

In each of the embodiments of FIGS. 1A to 18, the diapers are made by forming each of the components of the figures, for example the components 104, 107, 110, 111, 112, 114, and 117, assembling the components with suitable adhesives or other adhering means to achieve the arrangements shown, and then shaping them to the typical diaper shape. The order in which the components are formed or assembled may vary with the needs of the manufacturer.

A general manufacturing process may involve forming a liquid-impermeable backing sheet having an exterior surface and an interior surface so as to produce an exterior of the diaper and an interior of the diaper, forming a liquid-absorbing arrangement and placing the liquid-absorbing arrangement next to the backing sheet, forming an elastic pocket and bonding the pocket to the exterior surface of the backing sheet to contain a detector module, forming sensing electrodes and placing sensing electrodes within the interior of the diaper and within the interior surface of the backing sheet in contact with the liquid absorbing arrangement in a direction to extend opposite the elastic pocket so as to allow the sensing electrodes to couple capacitively to the detector module, assembling the various components by bonding, and forming the product into the shape of a diaper. The bonding of any component may occur at any phase of the process.

Figure 19:
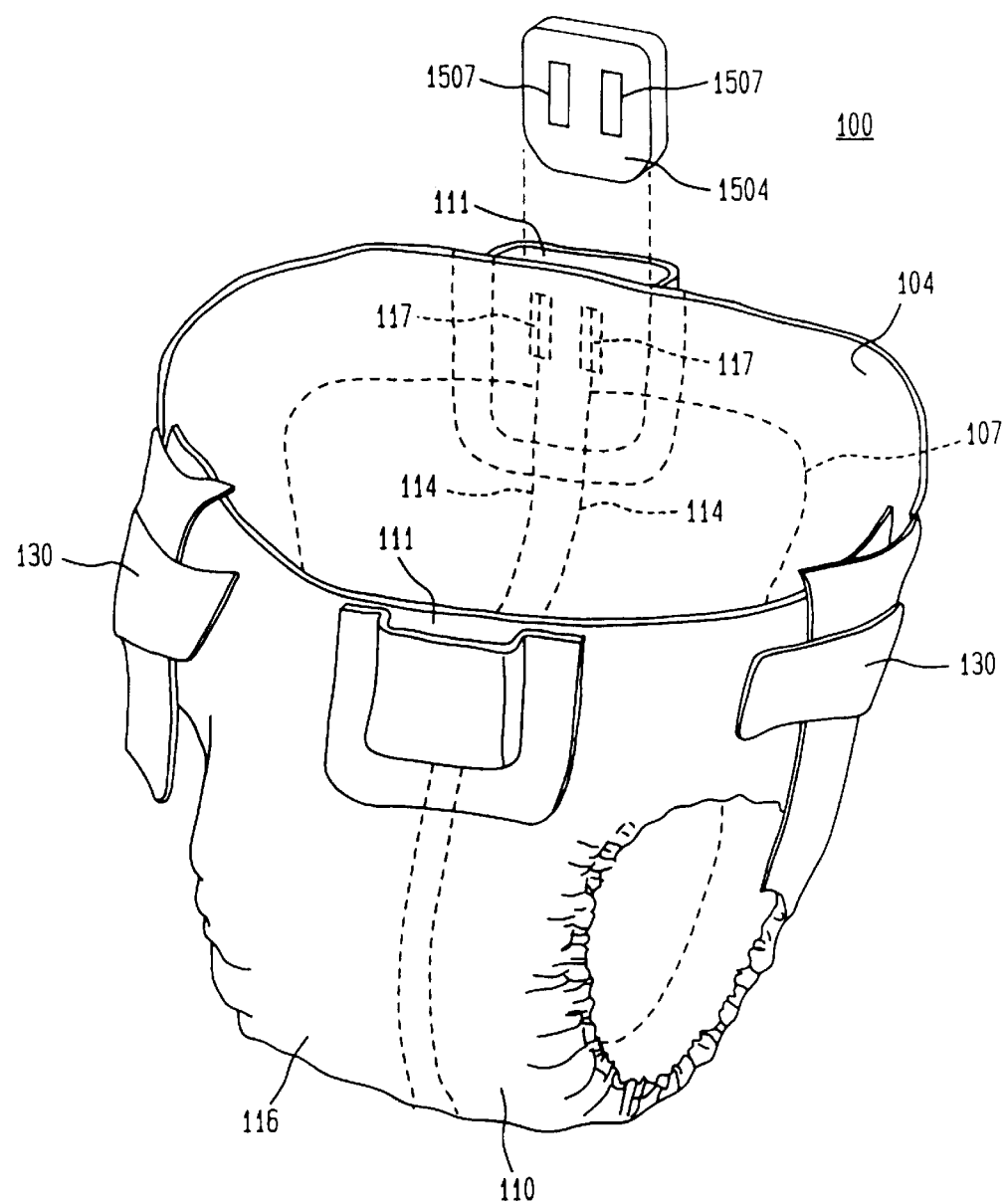
FIG. 19 is a perspective view of a diaper produced by the process of the invention.

Each of the elements formed and assembled are constructed to achieve the structure described for each of the figures and as described below. The process is finished by configuring the assembly into a diaper shape and adding elastics at the waist and legs and fastening strips 130 to produce the diaper of FIG. 19.

According to embodiments of the invention, diapers are manufactured by automatic machine where component materials are supplied from rolls or other sources located at points in the line. In one example, the backing sheet runs as a web through the full length of the manufacturing line up to the point where the individual diapers are separated from one another. However, the backing sheet may be put in sheets. The other components are affixed continuously, individually, or in partially pre-assembled combinations upon the backing sheet 110. In an exemplary machine direction assembly operation, at a point where the backing sheet web is fed in, the frontal tape is cut and placed onto the outer side of the backing sheet 110, and the pocket 111 is cut and bonded in place onto the outer side of the backing sheet 110. Adhesive is applied onto the area where the coupling electrodes 117 are to be placed, the sensing electrodes 114 are fed in, the coupling electrodes 117 are cut and placed, construction adhesive is applied to the entire surface, leg and waistband elastics are applied, and an absorbent pad 107 that was formed off line is carried between a web of tissue layer 109 and cover stock 104 and fed in and affixed, and the backing sheet 110 is cut to shape so as to narrow the crotch. Finally, the individual diapers are cut apart, separated, folded, and bagged. The order of these steps may change as desired.

Figure 20:
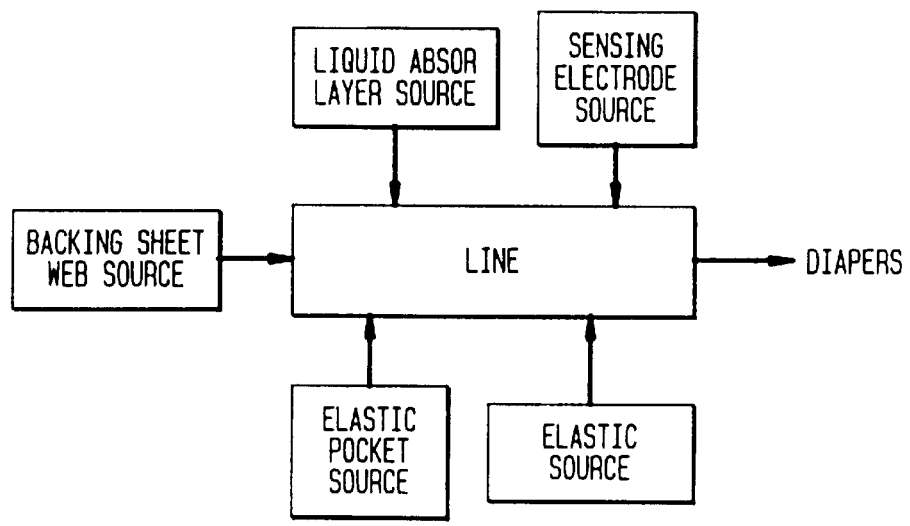
FIG. 20 is a schematic representation of a machine for constructing diapers.

An example of an automatic machine appears in FIG. 20. Here, a manufacturing line 2001 receives a web of material that forms the backing sheet, either pre-formed or uncut, from a backing sheet web source 2004. The line 2001 either moves the pre-formed backing sheets along the line or cuts the web to form the backing sheets. A liquid-absorber layer source 2007 supplies the components of the liquid-absorber layer, either individually or as a unit, either preformed or as linear sheets, to the line 2001. The line 2001 bonds the liquid-absorbing arrangement to the backing sheet made from the web. An elastic pocket source 2010 supplies an elastic pocket, pre-formed or uncut, to the line 2001 and the latter bonds the elastic pocket to the backing sheet made from the web. A sensing electrode source 2014 supplies sensing electrodes, in partially or completely shaped condition, to the line 2001 and the latter bonds them in the proper position in contact with the liquid-absorbing arrangement and opposite the pocket. An elastic source 2017 furnishes elastic to the line 2001, and the latter adds the elastic, and cuts and shapes the diapers into the state shown in FIG. 19. The line 2001 also separates, folds, and bags the diapers. According to various embodiments of the invention, each of the sources 2004, 2007, 2010, 2014, and 2017 assume different positions so that the order of processing may vary. The bonding may occur at phases of the process other than those shown. Also any one of the sources 2004, 2007, 2010, 2014, and 2017 may supply pre-formed or partially formed materials, and the line 2001 uses these material. Where the sources furnish incomplete or partially formed components, the line 2001 constructs the material into final forms.

Figure 21:
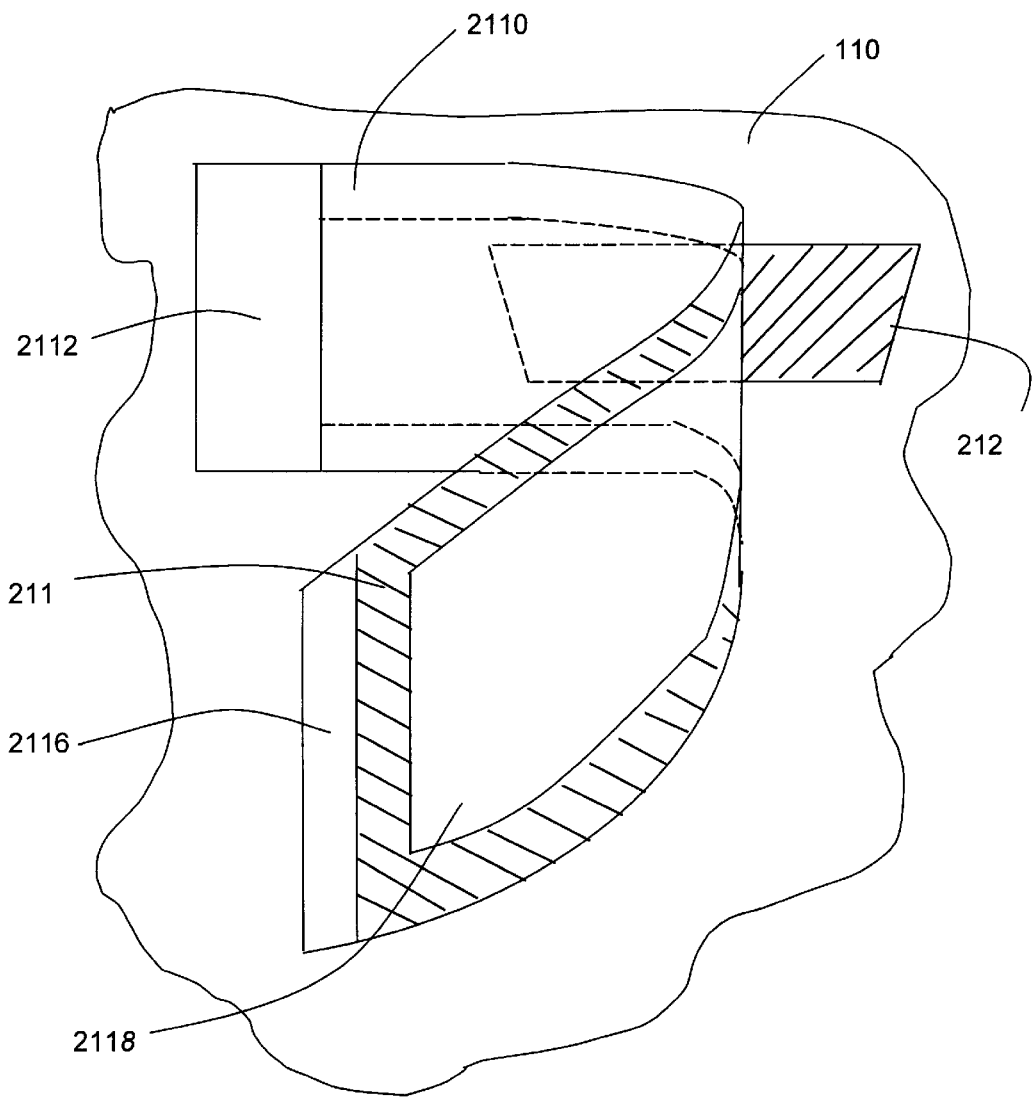
FIG. 21 is a plan view of a portion of an outer area of a diaper having a coated trapezoidal portion and a partially lifted covering flap.

FIG. 21, depicts an area of backing sheet 110, where an adhesive area 2120 is present primarily for the purpose of affixing a detector. In addition, when a cloth-like type of backing sheet 110 is employed, the adhesive serves to compact its outer fibers together, which improves the dielectric properties of the material in the critical coupling area, thereby increasing the degree of capacitive coupling. A covering flap 2110 is shown attached to backing sheet 110 in the bonding area 2112 at one of the edges of covering flap 2110. Alternatively, covering flap 2110 may be formed from a continuous extension of backing sheet 110 that extends from the waistband, avoiding the need to form covering flap 2110 from a separate piece of material.

Covering flap 2110 has at or near the three remaining edges of its border an adhesive zone 2114 on its surface opposite the backing sheet 110. This is a non-permanent adhesive that serves to hold the covering flap 2110 in place temporarily. Prior to use, covering flap 2110 serves to protect adhesive area 2120, and after placing a detector on adhesive area 2120, it serves to protect the detector from becoming dislodged. Release area 2118 prevents covering flap 2110 from becoming permanently affixed to adhesive area 2120. Clear area 2116 provides an area where the covering flap 2110 may be easily gripped for manipulation.

According to embodiments of the invention, the sensing electrodes are made as any one or more of the following:

filament, wire, yarn, ribbon, foil, fabric or film made from conductive material filament, yarn, ribbon, fabric or film that bears conductive filler material, that is coated with conductive material, or with surfaces subjected to a conversion process or suffused with a material that renders said surfaces conductive yarn that includes continuous or discontinuous lengths of conductive filament or wire, that is wrapped with conductive filament or wire, that is infused with material that is conductive, or that is infused with material that bears conductive filler material liquid or plastic material that is conductive or that bears conductive filler material, such as a thermoplastic, wax, paste, gel, latex, adhesive, or ink, that may be selectively applied onto a surface or into an absorbent matrix by methods such as printing, rolling, or extrusion selective conversion or suffusion of portions of a surface of a film, fabric or tissue material by a process that renders said portions conductive selective removal of continuous conductive coating or converted outer layer from surface of a film material such as by abrasion or photolithography to render multiple isolated conductive areas (electrodes) from a continuous piece of coated film selective removal of portions of an electrode film, fabric or tissue material such as by die-cutting to render multiple isolated conductive elements (electrodes) from a continuous element of coated film, fabric or tissue material electrodes may be in the form of a plurality of stripes each electrode may consist of a plurality of conductors.

According to embodiments of the invention, the attachment of the electrodes involves doing any one or more of the following:

selective coating or application of conductive material onto portions of a surface of a film, fabric or tissue material where said surface may be the backing sheet or where said film, fabric or tissue material may be subsequently applied onto said backing sheet incorporation into pad, tissue, or other component layer such as by weaving or laminating.

According to embodiments of the invention, the coupling electrodes are made as any one or more of the following:

ribbon, foil, fabric, tissue or film made from conductive material ribbon, fabric, tissue or film that bears conductive filler material, that is coated or infused with conductive material, or with surfaces subjected to a conversion process or suffused with a material that renders said surfaces conductive ribbon, fabric, tissue or film material that is conductive or has one or both surfaces made conductive, where said structure is optically transparent or translucent liquid or plastic material that is conductive or that bears conductive filler material, such as a thermoplastic, wax, paste, gel, latex, adhesive, or ink, that may be selectively applied onto a surface or into an absorbent matrix by methods such as printing, rolling, or extrusion selective conversion or suffusion of portions of a surface of a film, fabric or tissue material by a process that renders said portions conductive selective coating of portions of a surface of a film, fabric or tissue material with conductive material, such as by sputtering or thermal vapor deposition selective removal of continuous conductive coating or converted outer layer from surface of a film material to render multiple electrodes from a continuous piece of coated film selective removal of portions of an electrode film, fabric or tissue material such as by die-cutting to render multiple electrode elements from a continuous element of coated film electrodes may be in the form of a plurality of stripes.

According to an embodiment of the invention, connection of each coupling electrode to each sensing electrode are made as one or more of the following:

connection formed by conductive adhesive that is printed, transferred, thermally bonded or otherwise applied to the coupling electrode, the sensing electrode, or to another surface to which the electrodes are to be bonded connection formed by physical contact, where sensing electrode is interposed between a coupling electrode and another surface, where a non-conductive adhesive is applied to said other surface that holds said coupling electrode to said other surface connection optionally enhanced by presence of an electrically conductive liquid, paste, putty, or powdered solid material in contact with the sensing electrode and the coupling electrode According to an embodiment of the invention, combined sensing and coupling electrodes are made as one or more of the following:
- electrode pattern deposited or pre-assembled onto a carrier film, fabric or tissue, where pattern may be repeated continuously on a roll of material, either in the machine or cross directions, and where pattern may consist of pairs of sensing electrodes with coupling electrodes at one or both ends
  - when printed, the ink used for the sensing electrodes and the coupling electrodes may have different conductivity's
- electrodes that are uniform in width along their entire length
  - where diminished sensitivity to conditions external to the diaper may be attained by the placement of the electrodes so that one or more layers of dielectric material are interposed between the portion that will perform the sensing function and the backsheet
  - where the electrodes may be in the form of a plurality of stripes According to an embodiment of the invention, the pocket involves making it in one or more of the following ways:
- composed of an elastomeric or plastomeric, solid or foamed, film or fabric material to retain a substantially non-deformable item, or a substantially inelastic film or fabric material to retain a spring-loaded deformable item
  - transparent or opaque printing
    - with or without
    - superficial or sub-surface
- formed by bonding a relatively small patch of material along all but one of its edges
  - directly to the backsheet
  - to the bondable surface of a secondary patch of material, such as a label or frontal tape, that is applied to the backsheet
- reinforcement of the open edge by rolling and self-bonding an edge of the patch of material that will become the open edge prior to bonding onto a diaper or secondary patch of material
- reinforcement of the open edge by bonding a strip of reinforcing material to an edge of the patch of material that will become the open edge prior to bonding onto a diaper backsheet or secondary patch of material
- printing
  - on transparent material, forming a portion of a graphic that is completed or changed when the pocket is occupied by an object bearing a corresponding graphic
  - acts to obscure a view of the electrodes from the exterior of a diaper According to embodiments of the invention, the attachment of the pocket to the backsheet involves any one or more of the following steps:
- direct thermal or ultrasonic bonding;
- thermoplastic or thermosetting adhesive bonding
  - adhesive as coextruded skin on pocket material, selectively bonded,
  - adhesive selectively printed on pocket material; allows selective bonding by heating full area,
  - adhesive film co-laminated with pocket, selectively bonded
  - adhesive printed or sprayed onto pocket material and selectively bonded;
- bond directly to backsheet
- backsheet may be printed
  - forming a portion of a graphic that is completed or changed when the pocket is occupied by an object bearing a corresponding graphic,
  - acting to obscure a view of the electrodes from the exterior of a diaper;
- bond to a label that is applied to the backsheet label may be variously opaque to obscure view of electrodes,
  - variously opaque material,
  - variously opaque coating on transparent or variously opaque material,
  - label may be printed
    - forming a portion of a graphic that is completed or changed when the pocket is occupied by an object bearing a corresponding graphic,
    - acting to obscure a view of the electrodes from the exterior of a diaper;
- deformable module with a generally non-deformable pocket to achieve retention and tension;
- side levers on module
  - actuate one or more switches,
  - retain one or more batteries,
  - provide tensile force against sides of pocket.

According to embodiments of the invention, the control mechanisms operate any one or more of the following ways:
- interposition of a layer of water barrier film between the sensing electrodes and the absorbent material in the vicinity of the urine discharge area to prevent wetness from reaching said electrodes until the core is to some degree saturated;
- interposition of a layer of water-soluble, water barrier film between the sensing electrodes and the absorbent material to impart a time delay prior to when wetness reaches the sensing electrodes;
- alteration of the length or the spacing or both the length and spacing of the sensing electrodes to alter the degree to which the core must be saturated and the speed with which wetness reaches said electrodes.

According to embodiments of the invention, the structures and orientations involve assembling the components to achieve any one or more of the following sequences:
- backsheet/construction adhesive/sensing electrode/ film coupling electrode/core
- backsheet/PSA/sensing electrode/film coupling electrode/core
- backsheet/construction adhesive/sensing electrode/ film coupling electrode/tissue/core
- backsheet/PSA/sensing electrode/ film coupling electrode/tissue/core
- backsheet/PSA/film coupling electrode/sensing electrode/construction adhesive/tissue
- backsheet/printed coupling electrode/sensing electrode/construction adhesive/tissue According to embodiments of the invention, the methods for manufacture involve any one or more of the following steps:
- adjustment of the length of combined sensing and coupling electrodes to match various diaper lengths, where said combined electrodes are first deposited or pre-assembled onto a carrier film, fabric or tissue with coupling electrodes at both ends, said length adjustment executed by imparting a double fold, generally known as a Z-fold, across the carrier film, such as during or proximal to the process of cutting and placing the combined electrodes onto a diaper backsheet clear a swath in the conductive coating on the coupling electrode material to render multiple electrodes from a continuous piece of coated film
  using abrasion
    rotating frictive wheel, such as of rubber
    rotating abrasive wheel, such as of grit-coated aluminum
    rotating wire or fiber wheel, such as of brass or polyester
    one or more blade edges, oriented so as to scrape rather than slice the material surface
  using an electrical arc
  using a beam of light, such as from a laser
incorporate coupling electrodes into a diaper by unwinding electrode material from a roll or spool
  where coupling electrode material is slit, cut and placed
  where electrode material may bear a coating of conductive adhesive
  where another layer to which the coupling electrode is being applied may bear a coating of adhesive
  where the adhesive may be pressure-sensitive or thermally activated, transparent or variously opaque
incorporate coupling electrodes into a diaper by printing conductive ink onto backsheet
incorporate sensing electrodes into a diaper by unwinding electrode material continuously in-line with the backsheet in the case of diapers that are made in the machine direction
  where the electrode material is affixed to the backing sheet
    by laying it onto open construction adhesive previously applied to the backsheet
    by laying it onto the backsheet and keeping it in tension before the construction adhesive is applied
  where the sensing electrodes are severed between diapers
    by the same blade or blades that separate the diapers from one another
    by an electric current applied to a relatively short span of the sensing electrodes by knife edges in the region of the waistband
incorporate sensing electrodes into a diaper by cutting and placing lengths of electrode material
  where the electrode material is affixed to the backing sheet
    by laying it onto open construction adhesive previously applied to the backsheet
    by laying it onto the backsheet and keeping it in tension before the construction adhesive is applied
  where the lengths of electrode material are cut to length using one or more blades, water jets, flames, or beams of light, such as from a laser
remove the non-conductive fibers from segments of a continuous yarn containing or wrapped with one or more conductive fibers or wires
  by application of a flame
    where the flame height and intensity is modulated
    by direct modulation of the gas flow
      where the flow rate modulation is effected by control of a valving orifice plumbed in series with the gas flow
      where the flow rate modulation is effected by the motion of a piston in a cylinder or a diaphragm in a cavity that has a single inlet plumbed in parallel with the gas flow
    by modulation of the flow velocity of a cross-flowing jet of air
    by modulation of the flow into a cross-oriented vacuum inlet
    by a combination of the above
      where the flame is interrupted periodically by a perforated solid or mesh disk, while optionally the gas flow is simultaneously modulated
      where the flame is intermittently applied by moving the gas nozzle, while optionally the gas flow is simultaneously modulated
  by application of a jet of hot air (with similar approaches to modulation or interruption)
  by application of a modulated beam of light, such as from a laser
  by application of a jet of water where the jet is intermittently applied by moving the nozzle, while optionally modulating the flow simultaneously.

According to embodiments of the invention, the coating materials involve incorporating one or more of the following:
  metals for optically dense, electrically conductive coating, such as Ni, NiCr, Ni over Al, Sn
  semiconductive oxides to create an optically transparent, electrically conductive coating, such as ITO, ATO, ZnO
  multiple layers incorporating both metals and oxides to create an optically transparent, electrically conductive coating, such as $Al_2O_3$/Ag/ITO According to embodiments of the invention, the electrode materials are made as, or in any one or more of the following ways:
  fabric made electrically conductive by impregnation with one or more salts that remain wet, and therefore ionic and conductive, due to the hygroscopic nature of the mixture, such as of calcium chloride and sodium chloride, or lithium chloride and sodium chloride
  electrically conductive putty composed of a mixture of an electrically conductive filler and an oil base, optionally made stickier by the addition of one or more tackifiers, such as rosin.

According to other embodiments of the invention, the other aspects of the structure or method involve one or more of the following means or steps:
  coat surface of item to be placed into pocket with slippery coating, such as wax
  coat interior surfaces of pocket with slippery material, such as silicone oil.

What is claimed is:

1. A method of manufacturing a diaper, comprising:

forming a liquid-impermeable backing sheet having an exterior surface and an interior surface so as to form an exterior of the diaper and an interior of the diaper;

bonding a liquid-absorbing arrangement to the interior surface of the backing sheet;

bonding an elastic pocket to the exterior surface of the backing sheet to contain a detector module; placing sensing electrodes within the interior of the diaper and within the interior surface of the backing sheet in contact with the liquid absorbing arrangement that is bonded to the backing sheet, and in a direction to extend opposite the elastic pocket that is bonded to the exterior surface of the backing sheet so as to allow the sensing electrodes to couple only capacitively to the detector module.

2. A method as in claim 1, wherein bonding of the liquid absorbing arrangement includes placing a wetness-absorbing core layer on the liquid-impermeable backing sheet and placing a liquid-permeable film layer on the wetness-absorbing core layer.

3. A method as in claim 1, wherein placing the sensing electrodes includes bonding coupling electrodes forming a part of the sensing electrodes and having widened conductive areas on the ends of the sensing electrodes against the interior surface of the backing sheet opposite the elastic pocket.

4. A method as in claim 2, wherein bonding of the liquid absorbing arrangement includes placing a wetness distributing tissue layer between the liquid-impermeable backing sheet and the wetness-absorbing core layer and over the sensing electrodes.

5. A method as in claim 1, wherein bonding of the liquid absorbing arrangement includes placing a wetness-impermeable barrier between portions of the sensing electrodes and the core wetness-absorbing layer to define parts of the electrodes to be subject to contact with liquid.

6. A method as in claim 3, wherein placing sensing electrodes within the interior of the diaper and within the interior surface of the backing sheet includes assembling the sensing electrodes and the coupling electrodes with a sensor carrier and bonding the sensor carrier to the backing sheet.

7. A method as in claim 1, wherein placing sensing electrodes within the interior of the diaper and within the interior surface of the backing sheet includes forming pluralities of pairs of sensing electrodes in a continuous line and separating the pairs of sensing electrodes from the other pairs before placing each pair of sensing electrodes in a diaper.

8. A method as in claim 1, wherein placing sensing electrodes within the interior of the diaper and within the interior surface of the backing sheet includes forming the sensing electrodes by selective removal of continuous conductive coating or converted outer layer from surface of a film material to render multiple isolated conductive areas from a continuous piece of coated film.

9. A method as in claim 1, wherein placing sensing electrodes within the interior of the diaper and within the interior surface of the backing sheet includes forming each sensing electrode from a plurality of parallel filamentary elements.

10. A method as in claim 1, wherein placing sensing electrodes within the interior of the diaper and within the interior surface of the backing sheet includes forming the sensing electrodes of filamentary elements in contact with flat conductors forming the coupling electrodes nipped down against the sensing electrode with the tissue layer nipped down over said sensing and said coupling electrodes and the core layer nipped down over the tissue layer and the tissue layer nipped down over the core layer.

11. A method as in claim 1, wherein placing sensing electrodes includes placing an electrically conductive material in spaces adjacent the sensing electrodes.

12. A method as in claim 1, wherein placing sensing electrodes within the interior of the diaper and within the interior surface of the backing sheet includes incorporating the sensing electrodes within the liquid absorbing arrangement.

13. A method as in claim 2, wherein placing sensing electrodes within the interior of the diaper and within the interior surface of the backing sheet includes incorporating the sensing electrodes within the wetness-absorbing core layer and extending the ends of the electrodes outside of the wetness absorbing core layer between the wetness-absorbing core layer and the liquid-impermeable backing sheet.

14. A method as in claim 1, wherein placing sensing electrodes within the interior of the diaper and within the interior surface of the backing sheet includes forming the sensing electrodes by abrading portions of a conductive layer from a ribbon of non-conductive material carrying a conductive layer.

15. A method as in claim 1, wherein placing sensing electrodes within the interior of the diaper and within the interior surface of the liquid-impermeable backing sheet includes forming the sensing electrodes by placing conductive filaments on an adhesive on a backing layer.

16. A method as in claim 1, wherein placing sensing electrodes within the interior of the diaper and within the interior surface of the backing sheet includes forming the sensing electrodes by spin wrapping wire about a yarn.

17. A method as in claim 1, wherein forming the backing sheet includes forming the backing sheet from two overlying bonded components and treating a portion at the pocket to make the portion at the pocket thinner than the remainder of the backing sheet.

18. A method as in claim 17, wherein treating a portion of the backing sheet at the pocket includes ultrasonic treatment.

* * * * *